United States Patent [19]

Nishino et al.

[11] Patent Number: 6,029,501
[45] Date of Patent: Feb. 29, 2000

[54] VIBRATION TYPE GAS DENSITOMETER

[75] Inventors: Hiroshi Nishino; Junichi Suzuki; Shigeo Yasuda; Mitsuhiko Sasaki; Ryuichi Kawamura, all of Tokyo, Japan

[73] Assignee: Yokogawa Electric Corporation, Tokyo, Japan

[21] Appl. No.: 09/194,708

[22] PCT Filed: Mar. 27, 1998

[86] PCT No.: PCT/JP98/01404

§ 371 Date: Dec. 15, 1998

§ 102(e) Date: Dec. 15, 1998

[87] PCT Pub. No.: WO98/45681

PCT Pub. Date: Oct. 15, 1998

[30] Foreign Application Priority Data

| Apr. 4, 1997 | [JP] | Japan | 9/086237 |
| Apr. 4, 1997 | [JP] | Japan | 9/086238 |
| Apr. 4, 1997 | [JP] | Japan | 9/086240 |
| Apr. 4, 1997 | [JP] | Japan | 9/086241 |

[51] Int. Cl.$^7$ .................................................... G01N 9/00
[52] U.S. Cl. ............................................ 73/32 A; 73/702
[58] Field of Search .................... 73/32 A, 579, 73/702, 704, 721, 727, 862.59

[56] References Cited

U.S. PATENT DOCUMENTS

| 4,429,564 | 2/1984 | Ikeda et al. | 73/32 A |
| 4,495,818 | 1/1985 | Ikeda et al. | 73/32 A |

FOREIGN PATENT DOCUMENTS

| 1-57144 | 3/1989 | Japan | 73/32 A |
| 64-84132 | 3/1989 | Japan . | |
| 4296635 | 10/1992 | Japan . | |
| 2187286 | 9/1987 | United Kingdom | 73/32 A |

*Primary Examiner*—Hezron Williams
*Assistant Examiner*—Helen C. Kwok
*Attorney, Agent, or Firm*—Moonray Kojima

[57] ABSTRACT

A vibration gas density meter provided with a cylindrical resonator, a cylinder block that incorporates the above cylindrical resonator concentrically and has one end of the cylindrical resonator fixed to itself, and a case which concentrically incorporates the above cylinder block and supports both ends of the cylinder block, further comprising first and second elastic elements which are provided between both end faces of the cylinder block and the case respectively, and through which the cylinder block is supported by the case in the direction of cylindrical axis, sealing the gaps between the cylinder block and the case as well, and third and fourth elastic elements which are provided between both parts of the outer cylindrical surface on both end face sides of the above cylinder block and the case respectively and through which the cylinder block is supported by the case in the radial direction, sealing the gaps between the cylinder block and the case as well.

10 Claims, 5 Drawing Sheets

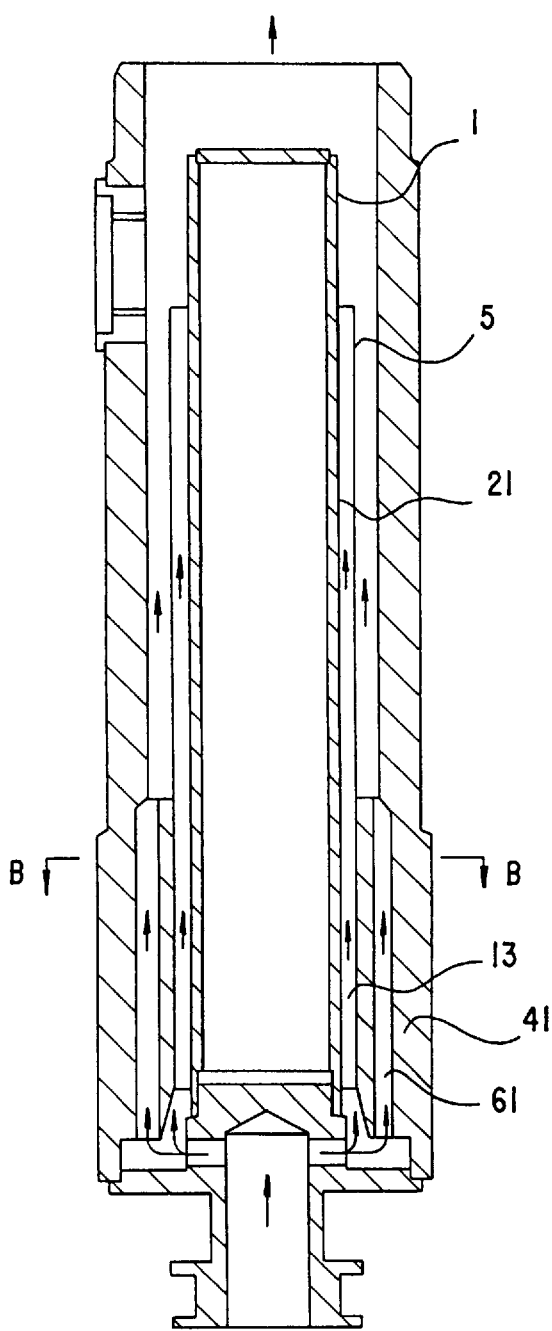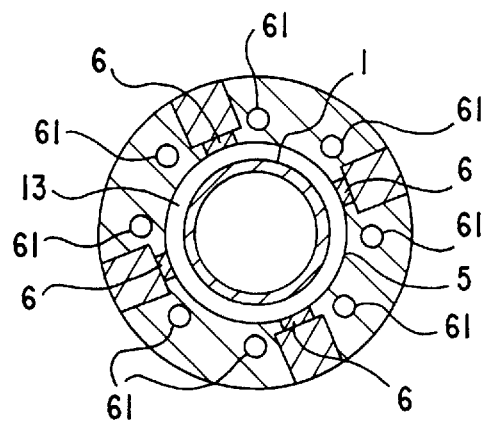

VIBRATION TYPE GAS DENSITOMETER

BACKGROUND OF THE INVENTION

1. Field of the Invention

First, the present invention relates to a vibration gas density meter in which anti-vibration properties are improved, no specific anti-vibration measures are necessary, and the intrinsically safe explosion-protected construction is easily adopted.

Second, the present invention relates to a vibration gas density meter in which its temperature characteristics are improved, no specific heat-insulating measures are necessary, and the intrinsically safe explosion-protected construction is easily adopted.

Third, the present invention relates to a vibration gas density meter in which its ambient temperature characteristics are improved.

Fourth, the present invention relates to a vibration gas density meter in which its sensitivity is improved and the pressure loss is less.

2. Description of the Prior Art

FIG. 1 shows a drawing to illustrate the configuration of an embodiment of the prior art generally used to date. This drawing is, for example, shown on page 4 of the catalog titled "DG8 type Gas Density Meter," published on Jul. 15, 1990, by Yokogawa Electric Corporation.

FIG. 2 shows an A—A cross sectional drawing for FIG. 1, and FIGS. 3 and 4 are drawings for explaining operations of the embodiment indicated in FIG. 1.

In FIG. 1 and FIG. 2, numeral 1 shows the center block provided to avoid requiring a large flow of a sample gas.

Numeral 2 shows a resistance thermometer embedded in center block 1.

Numeral 3 shows an inside cylinder incorporating resistance thermometer 2 concentrically.

Numeral 4 shows an outside cylinder incorporating inside cylinder 3 concentrically.

Numeral 5 shows a thin wall cylindrical resonator provided between inside cylinder 3 and outside cylinder 4 concentrically.

Numeral 6 shows vibratory elements to excite cylindrical resonator 5. In this case, piezo-electric elements are used.

Numeral 7 shows a case incorporating outside cylinder 4.

Numeral 8 shows a sleeve to fix one end of outside cylinder 4 to case 7. In this case, rigid tetra-fluoro-ethylene (teflon) is used for sleeve 8.

Numeral 9 shows the O-ring 1 that seals the gap between outside cylinder 4 and sleeve 8.

Numeral 11 shows the O-ring 2 that seals the gap between sleeve 8 and case 7.

Numeral 12 shows a piece of vibration-proof rubber through which the other end of outside cylinder 4 is fixed to case 7.

Numeral 13 shows a ring-shaped inside flow way of the resonator that is provided inside bottom block 14 of outside cylinder 4 and that supplies a sample gas to the inner cylindrical surface of cylindrical resonator 5.

Numeral 15 shows the outside flow ways of the resonator that supply a sample gas to the outer cylindrical surface of cylindrical resonator 5. These outside flow ways of the resonator are provided through bottom block 14 of outside cylinder 4 and are arranged on a circumference at the outside of inside flow way of resonator 13 avoiding vibratory elements 6. In this case, four flow ways are provided.

In the above configuration, as shown in FIGS. 3 and 4, the sample gas enters inside cylinder 3, turns back at the lower end of inside cylinder 3, and enters bottom block 14 of outside cylinder 4. The sample gas is then branched to inside flow way of resonator 13 and the outside flow ways of resonator 15. The sample gas then passes along the inner and outer cylindrical surfaces of cylindrical resonator 5 and flows out of outside cylinder 4.

The density of a sample gas is determined by measuring the resonance frequency of cylindrical resonator 5 by utilizing the fact that the resonance frequency of cylindrical resonator 5 varies with the density of gas around cylindrical resonator 5.

However, in such a device, (1) Outside cylinder 4 is supported by case 7 through sleeve 8 and vibration-proof rubber 12.

Accordingly, outside cylinder 4 was provided with general anti-vibration measures against case 7. However, since sufficient vibration-resistant construction was not considered, vibration propagated from case 7 or the gas piping for introducing a sample gas. For this reason, if vibration disturbance was strong, additional anti-vibration measures were necessary.

In addition, if vibration of the piping was strong, metal pipes could not be used but pipes made of a material of polyethylene or the like had to be used, and so the gases that could be measured were limited, which was a problem.

Also, since outside cylinder 4 was electrically insulated from case 7, an intrinsically safe explosion-protected construction could be obtained but that construction was complex and the manufacturing cost was high.

(2) Outside cylinder 4 was supported by case 7 through sleeve 8 and vibration-proof rubber 12.

Accordingly, outside cylinder 4 was provided with general heat insulation measures against case 7. However, since the heat-insulated construction sufficient to gain high sensitivity was not considered, heat was conducted from case 7 or the gas piping for introducing a sample gas. For this reason, if ambient temperature changes are violent, specifically if good transient characteristics against sudden temperature changes were to be achieved, additional heat-insulating measures were necessary.

In addition, if ambient temperature changes were violent, heat-insulating measures were necessary, such as housing the meter in a constant temperature oven, placing it in anti-freeze solution, or installing it in an air-conditioned room and others. Such were the problems.

Also, since outside cylinder 4 was electrically insulated from case 7, an intrinsically safe explosion-protected construction could be obtained but that construction was complex and the manufacturing cost was high.

(3) Resistance thermometer 2 for temperature compensation is embedded in center block 1. The sample gas, after passing through the gap between center block 1 and inside cylinder 3, reaches the inner and outer cylindrical surfaces of cylindrical resonator 5.

Since center block 1 consists of metal, its heat capacity is large and so the temperature of center block 1 itself is less affected by transient changes due to changes in external atmospheric temperature and so forth.

While, because the heat capacity of the sample gas is small, heat is exchanged between the sample gas and center block 1 when the sample gas passes through the gap between inside cylinder 3 and center block 1. When the sample gas reaches cylindrical resonator 5, the temperature of the sample gas attains approximately the temperature of center block 1.

Accordingly, resistance thermometer 2 is used to compensate the temperature for the sample gas for the reason that, although resistance thermometer 2 measures the temperature of center block 1, the temperature of the sample gas is also equivalent to that of center block 1.

However, in such a system, if a higher sensitivity-vibration gas density meter is required, its temperature characteristics also need to be more stable and the above-described construction is not appropriate.

(a) That is, due to thermal inflow through outside cylinder 4 from case 7, there occurs a difference between the temperature of cylindrical resonator 5, i.e. the sample gas, and the temperature measured with resistance thermometer 2 in center block 1.

(b) In addition, since resistance thermometer 2 is located in center block 1, it cannot detect the change in the temperature of cylindrical resonator 5 and the sample gas for thermal inflow from outside due to the large heat capacity of center block 1.

For the above reasons, more accurate temperature compensation cannot be obtained in measuring the density of the sample gas.

(4)

(a) Four outside flow ways of resonator 15 are provided on a circumference at the outside of the inside flow way of resonator 13.

However, if a higher sensitivity-vibration gas density meter is to be developed, it is clear that stagnant parts of the sample gas generated between each two of the four outside flow ways of resonator 15 have an adverse effect on the response characteristics of cylindrical resonator 5.

(b) Assuming that the gas density meter is directly inserted into the piping for measurement, it has been designed such that the sample gas inlet and outlet are located near to each other. However, this cannot but turn back the stream of sample gas, increasing the pressure loss.

If the pressure loss increases, the sample gas used for density measurement is vented into the atmosphere or the like as exhaust gas due to the pressure drop. This goes against the recent trend toward protection of the global environment.

In addition, the stream of the sample gas is lengthened corresponding to the length of resistance thermometer 2 to obtain the effective temperature compensation by temperature detection with resistance thermometer 2, but this also causes the pressure loss.

(c) Since center block 1, inside cylinder 3, cylindrical resonator 5 and outside cylinder 4 are assembled concentrically, the construction is complicated and the machining and assembling costs are high.

SUMMARY OF THE INVENTION

The objectives of the present invention are:

(1) First, to provide a vibration gas density meter in which anti-vibration properties are improved, no specific anti-vibration measures are necessary, and the intrinsically safe explosion-protected construction is easily adopted.

(2) Second, to provide a vibration gas density meter in which the temperature characteristics are improved, no specific heat-insulating measures are necessary, and the intrinsically safe explosion-protected construction is easily adopted.

(3) Third, to provide a vibration gas density meter that has improved ambient temperature characteristics.

(4) Fourth, to provide a vibration gas density meter in which the sensitivity is improved and the pressure loss is less.

In order to achieve the above objectives, the present invention provides the following vibration gas density meters:

(1) A vibration gas density meter provided with a cylindrical resonator; a cylinder block concentrically incorporating the cylindrical resonator so that one end of the cylindrical resonator is fixed to the bottom block of the cylinder block in a cantilever-like manner and the other end of the cylindrical resonator is open-ended; vibratory elements that excite the cylindrical resonator provided at the bottom block of the cylinder block; an inside flow way of the resonator whose cross section is ring-shaped, provided at the bottom block of the cylinder block supplying the sample gas to the inner cylindrical surface of the cylindrical resonator; outside flow ways of the resonator provided through the bottom block of the cylinder block, arranged on an outside circumference of the above inside flow way of the resonator avoiding the above vibratory elements, supplying the sample gas to the outer cylindrical surface of the cylindrical resonator; and a case concentrically incorporating the cylinder block and supporting the cylinder block at both its ends; further comprising the first and second elastic elements that are provided between both end faces of the cylinder block and the case respectively, and through which the cylinder block is supported by the case in the direction of cylindrical axis, sealing the gaps between the cylinder block and the case as well, and the third and fourth elastic elements that are provided between both parts of the outer cylindrical surface on both end face sides of the cylinder block and the case respectively and through which the cylinder block is supported by the case in the radial direction, sealing the gaps between the cylinder block and the case as well.

(2) A vibration gas density meter mentioned in (1), further provided with an introduction pipe, one end of which is connected to the sample gas introducing port side of the cylinder block, the other end of which is connected to the case, and which introduces the sample gas into the cylinder block as well as prevents heat transfer from the case to the cylinder block by having a predetermined length.

(3) A vibration gas density meter mentioned in (1) or (2), further comprising first and second concavities provided at both end faces of the case respectively, first and second elastic elements that are provided between the above first and second concavities and the cylinder block respectively and through which the cylinder block is supported by the case in the direction of cylindrical axis, sealing the gaps between the first and second concavities and the cylinder block as well, and third and fourth elastic elements that are provided between both parts of the cylindrical surface on both end face sides of the cylinder block and the first and second concavities respectively and through which the cylinder block is supported by the case in the radial direction, sealing the gaps between the cylinder block and the first and second concavities as well.

(4) A vibration gas density meter mentioned in any of (1) to (3), wherein O-rings are used as the first, second, third, and fourth elastic elements.

(5) A vibration gas density meter mentioned in any of (2) to (4), comprising heat insulation composed of heat-insulating material provided in part of the gaps or the entire gaps between the cylinder block and the case.

(6) A vibration gas density meter mentioned in any of (2) to (5), comprising heat insulation composed of heat-insulating material provided around the above introduction pipe.

(7) A vibration gas density meter mentioned in (1), wherein a resistance thermometer mounted on the cylindrical surface of the cylinder block is provided with a resistance element arranged in the vicinity of the open end of the cylindrical resonator.

(8) A vibration gas density meter mentioned in (7), wherein the above resistance element is arranged in the vicinity of the downstream of the above open-end surface of the cylindrical resonator.

(9) A vibration gas density meter mentioned in (1), comprising outside flow ways of the resonator provided through the bottom block of the cylinder block by a predetermined number so that a stagnant part of the sample gas is not generated when the sample gas is supplied to the outer cylindrical surface of the cylindrical resonator, a sample gas introduction way, one end of which is provided at the case on the bottom block side of the cylinder block and the other end of which is communicated with the predetermined number of outside flow ways of the resonator and the inside flow way of the resonator, and a sample gas discharge way through which the sample gas is discharged, one end of which is provided at the case on the side opposite to the bottom block of the cylinder block and the other end of which is communicated with a port on the above described side of the cylinder block.

In the above configuration, the sample gas is introduced into the cylinder block, passes along the inner and outer cylindrical surfaces of the cylindrical resonator, and is discharged from the case.

The density of sample gas can be determined by measuring the resonance frequency of the cylindrical resonator utilizing the fact that the resonance frequency of the cylindrical resonator varies with the density of the gas surrounding the cylindrical resonator.

The cylinder block is supported by the case through the first, second, third, and fourth elastic elements.

As a result, (1) As described above, the cylinder block is supported by the case through the first, second, third, and fourth elastic elements and thus is completely floating from the case. Thus, a vibration gas density meter that has improved anti-vibration characteristics and that has enhanced noise immunity over a wide frequency range, can be obtained.

(2) Accordingly, a vibration gas density meter that has lower installation cost, such as for selection of and limitation to pieces of vibration-proof rubber, anti-vibration construction, and installation locations, and for plastic piping work, can be obtained without requiring anti-vibration measures in the case of intense vibration disturbance.

(3) The cylinder block is supported by the case through the first, second, third and fourth elastic elements, and thus is completely floating from the case. Thus, a vibration gas density meter that is easily electrically insulated from the ground and is ready for the adoption of intrinsically safe explosion-protected construction can be obtained by employing an electrical insulation material for the first, second, third, and fourth elastic elements.

(4) If the cylinder block is supported by the first and second concavities provided in the case through the first, second, third, and fourth elastic elements, a vibration gas density meter whose cylinder block is securely supported by the case can be obtained.

(5) If O-rings are used for the first, seconds third, and fourth elastic elements, the cylinder block can be heat-insulated from the case, and thus a vibration gas density meter that has good temperature characteristics can be obtained.

(6) If O-rings are used for the first, second, third, and fourth elastic elements, the construction can be made simple, and thus a vibration gas density meter that has lower manufacturing cost can be obtained.

Consequently, according to the present invention, a vibration gas density meter that has improved anti-vibration characteristics, and which requires no specific vibration measures and can easily adopt the intrinsically safe explosion-protected construction, can be obtained.

Next, according to the invention (2), the cylinder block is supported by the case through the first, second, third, and fourth elastic elements.

In addition, heat transfer from the case on the sample gas entry side to the cylinder block is greatly reduced by the introduction pipe.

Further, heat transfer from the case on the sample gas entry side to the cylinder block is prevented by the heat insulation.

As a result, (1) The cylinder block is supported by the case through the first, second, third, and fourth elastic elements, and thus is completely floating from the case. At the same time, heat transfer from the case on the sampling gas entry side to the cylinder block is greatly reduced by the introduction pipe. Therefore, the cylinder block is heat-insulated from the case and so a vibration gas density meter that has improved temperature characteristics can be obtained.

Specifically, a vibration gas density meter in which the transient characteristics at sudden temperature changes are greatly improved and which can enhance the control characteristics in various applications, especially in calorie control for city gas, can be obtained.

(2) Accordingly, if ambient temperature changes are large, it is no longer necessary to take specific heat-insulation measures, for example, such as housing the meter in a thermostatic oven, installing the meter in anti-freeze solution, or installing the meter in an air-conditioned room. Thus, a vibration gas density meter that has lower installation cost is obtained.

(3) The cylinder block is supported by the case through the first, second, third and fourth elastic elements, and thus is completely floating from the case. Thus, a vibration gas density meter that is easily electrically insulated from the ground and is ready for the adoption of intrinsically safe explosion-protected construction can be obtained by employing an electrical insulation material for the first, second, third, and fourth elastic elements.

(4) If the cylinder block is supported by the first and second concavities provided in the case through the first, second, third, and fourth elastic elements, a vibration gas density meter whose cylinder block is securely supported by the case can be obtained.

(5) If O-rings are used for the first, second, third, and fourth elastic elements, the cylinder block can be heat-insulated from the case, and thus a vibration gas density meter that has further good temperature characteristics can be obtained.

(6) If O-rings are used for the first, second, third, and fourth elastic elements, the construction can be made simple, and thus a vibration gas density meter that has lower manufacturing cost can be obtained.

(7) If the heat insulation is provided around the introduction pipe, heat transfer from the case on the sample gas entry side to the cylinder block is prevented. Thus, a vibration gas density meter that has improved temperature characteristics can be obtained.

Consequently, according to the present invention, a vibration gas density meter that has improved temperature characteristics, and which requires no specific heat-insulation measures and can easily adopt the intrinsically safe explosion-protected construction, can be obtained.

Next, according to invention (7), since the heat capacity of the sample gas is small, the sample gas exchanges heat with the cylindrical resonator when it passes along the inner and outer cylindrical surfaces of the cylindrical resonator. Therefore, the temperature of the sample gas becomes equal to the temperature of the cylindrical resonator at its open end.

Also, while the sample gas is passing, the resistance element can detect the temperature change of the cylindrical resonator due to inflow of heat from the outside.
As a result, (1) The resistance thermometer is mounted on the cylindrical surface of the cylinder block and the resistance element is arranged in the vicinity of the open end of the cylindrical resonator. Thus, a vibration gas density meter that can detect the changes in ambient temperature and can appropriately compensate for the ambient temperature can be obtained.

(2) In addition, if the resistance element is arranged close to the downstream of the open-end surface of the cylindrical resonator, changes in ambient temperature can also be detected. Further, since temperatures are measured in a position where temperatures of the cylindrical resonator and the sampling gas just balance, a vibration gas density meter that can detect ambient temperature changes and further can compensate for the ambient temperature accurately and appropriately, can be obtained.

Consequently, according to the present invention, a vibration gas density meter that has improved ambient temperature characteristics can be obtained.

Further, according to the invention (9), the sample gas is introduced into the cylinder block through the sample gas introduction way and branched to the inside flow way of the resonator and eight outside flow ways of the resonator. The sample gas is then discharged from the sample gas discharge way after passing along the inner and outer cylindrical surfaces of the cylindrical resonator.
As a result, (1) The outside flow ways of resonator are provided through the bottom block of the cylinder block by the predetermined number so that a stagnant portion of the sample gas is not generated when the sample gas is supplied to the outer cylindrical surface of the cylindrical resonator. Accordingly, contamination of the sample gas is eliminated, and thus a vibration gas density meter that has improved response characteristics and high sensitivity can be obtained.

(2) Provision of the inlet and outlet of the sample gas close to each other is abandoned so that the density meter can be directly inserted into a measurement piping, and the sample gas introduction way is provided on the one end side of the cylinder block and the sample gas discharge way is provided on the other end side of the cylinder block. Since, as shown above, turn-back of the sample gas passage is discontinued, the passage resistance decreases and so the pressure loss is reduced.

Further, since a predetermined number of outside flow ways of resonator that do not generate a stagnant part of the sample gas are provided, the pressure loss is further reduced.

For this reason, gas density can be measured even if the differential pressure between the input and output of a vibration gas density meter is small. So, since a vibration gas density meter can be placed in a cycling system for a measuring object, a specific sampling system becomes unnecessary. Thus, a vibration gas density meter that has lower installation cost can be obtained.

In particular, a vibration gas density meter suitable for measurement of dangerous sample gas can be obtained, for example, for measuring the concentration of hydrogen in hydrogen-cooled generators.

(3) Furthermore, since the pressure loss in the vibration gas density meter is small, gas density can be measured even if the differential pressure between the input and output of the vibration gas density meter is small. This eliminates the necessity to keep the sample gas at the output of a vibration gas density meter at low pressure. Thus, the sample gas whose measurement has finished can be easily returned to a place where the fluid can be reused, and does not need to be disposed of by being vented into the atmosphere as an exhaust gas, and thus is consistent with the recent trend toward protection of the global environment. Hence, a vibration gas density meter that has lower operation cost can be obtained.

Specifically, for example, a vibration gas density meter suitable for an application that, in a calorie adjustment line for liquefied natural gas (LNG), LNG after being used for measurement can be returned to a line from which the LNG was sampled, can be obtained.

Consequently, according to the present invention, a vibration gas density meter that has improved sensitivity and lower pressure loss can be realized.

BRIEF DESCRIPTION OF THE DRAWINGS

FIG. 6 shows a detailed drawing indicating the essential parts of the embodiment illustrated in FIG. 5.

FIG. 7 shows the B—B cross sectional drawing of FIG. 6.

DESCRIPTION OF THE PREFERRED EMBODIMENT

The present invention will be described in detail below using the drawings.

Figure 5:
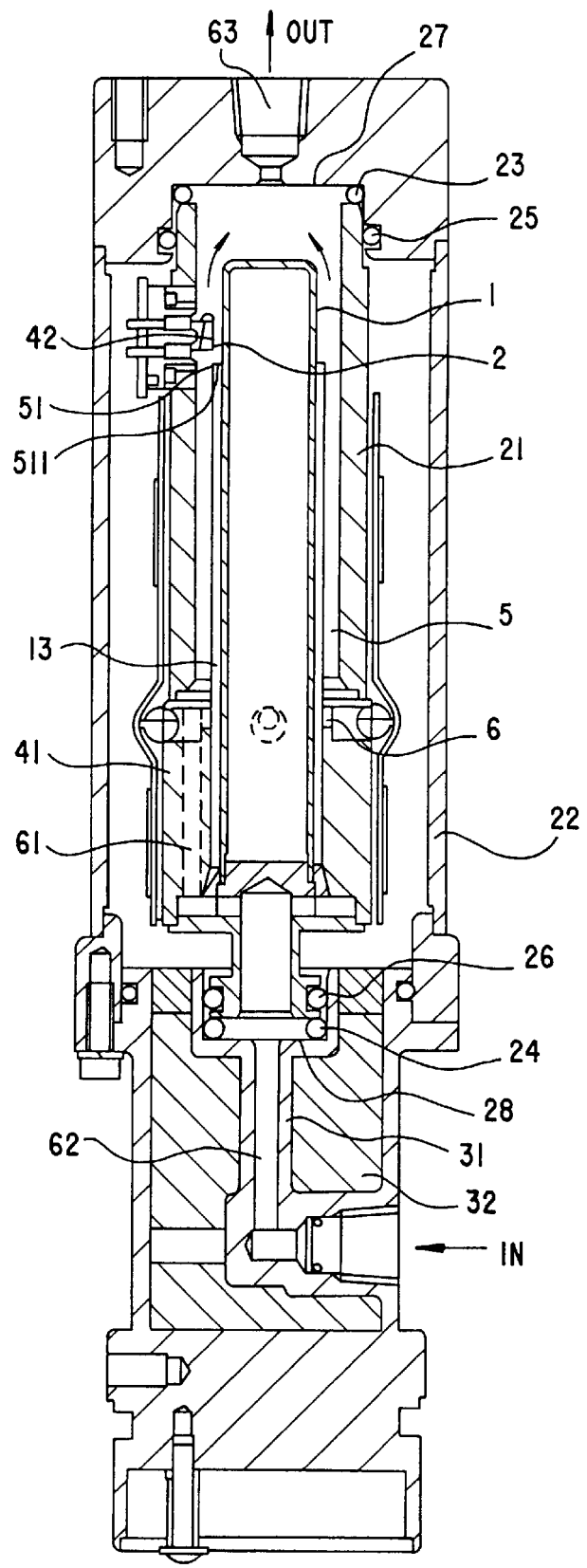
FIG. 5 shows a drawing explaining the configuration of an embodiment of the present invention.

FIG. 5 shows a drawing explaining the configuration of the essential parts of an embodiment of the present invention. FIG. 6 shows a detailed drawing indicating the essential parts of the embodiment illustrated in FIG. 5. FIG. 7 shows the B—B cross sectional drawing of FIG. 6.

Figure 1:
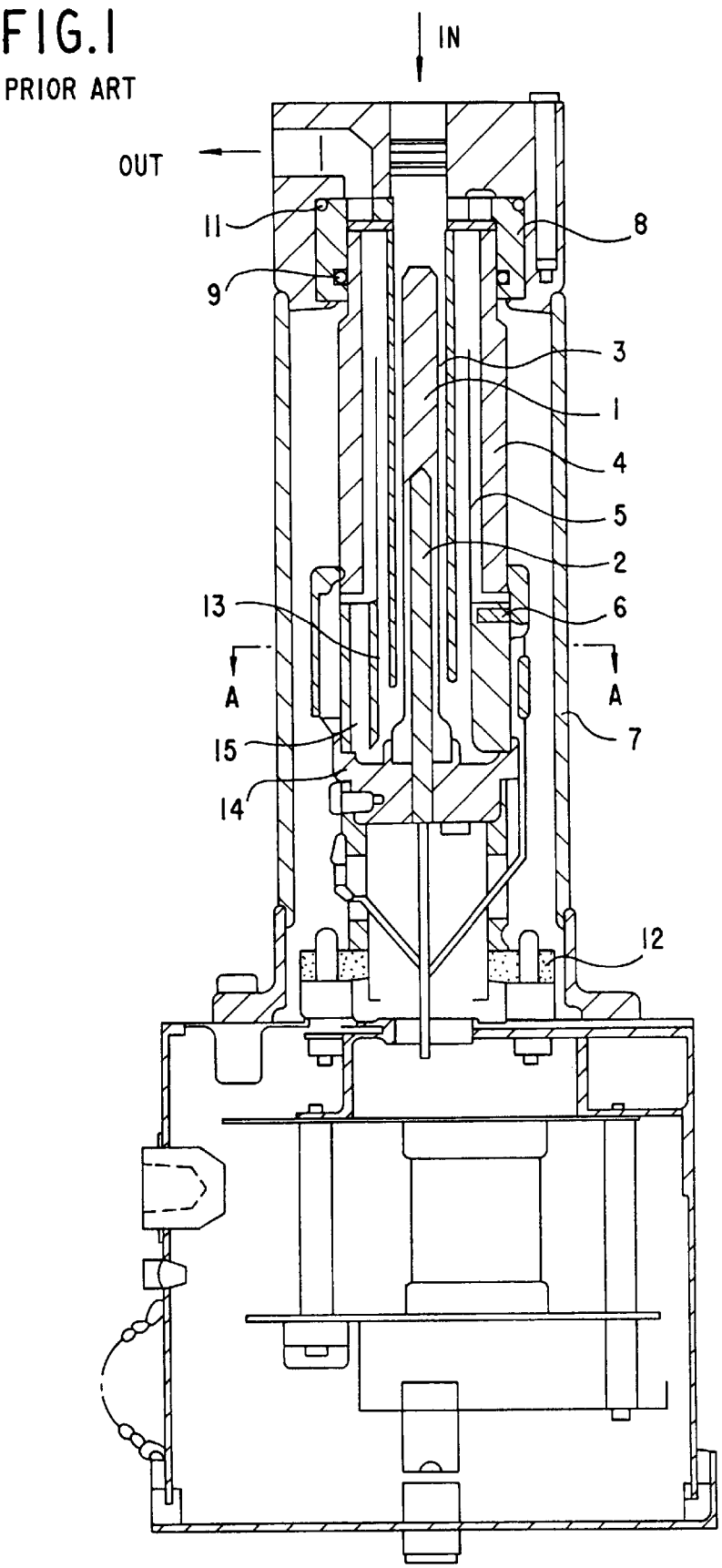
FIG. 1 shows a drawing explaining the configuration of an embodiment of the prior art used to date.
Figure 2:
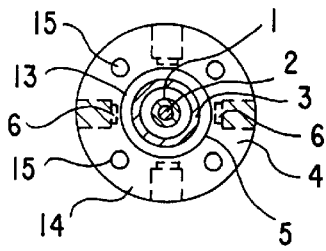
FIG. 2 shows the A—A cross sectional drawing of FIG. 1.
Figure 3:
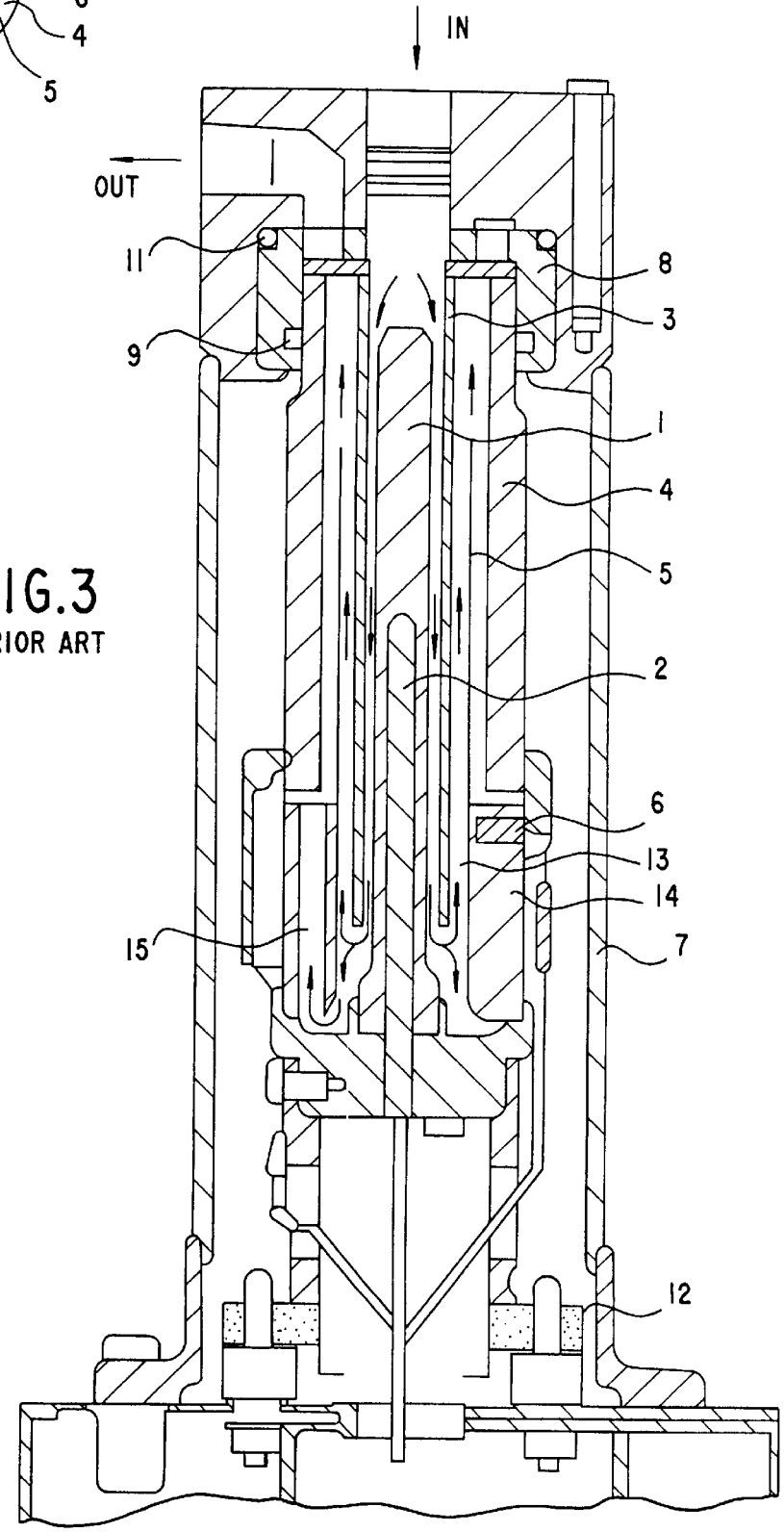
FIG. 3 shows a drawing explaining operations of the embodiment illustrated in FIG. 1.
Figure 4:
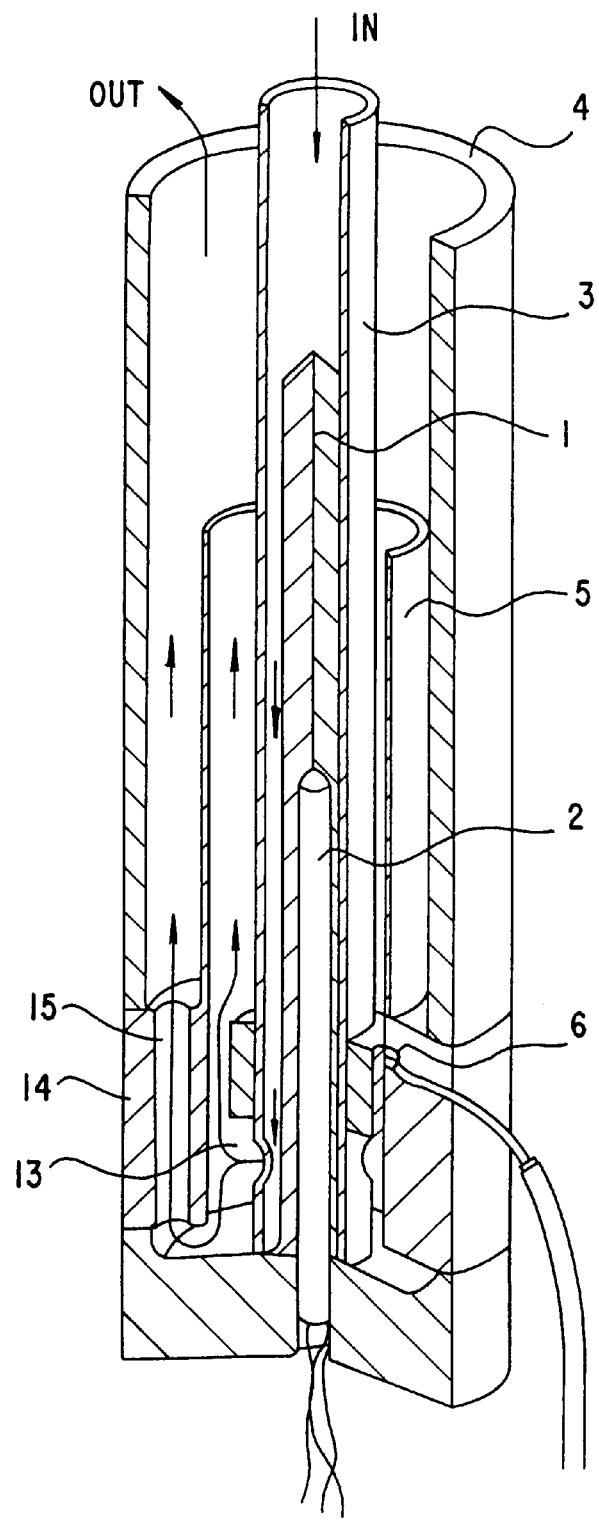
FIG. 4 shows a drawing explaining the operating principle of the embodiment illustrated in FIG. 1.

In these figures, the same symbols as those in FIG. 1 represent the same functions. In the following, only the portions different from that in FIG. 1 will be described.

Numeral 21 shows a cylinder block in which cylindrical resonator 5 is incorporated concentrically and to which one end of cylindrical resonator 5 is fixed on the side of bottom block 41.

Numeral 22 shows a case that concentrically incorporates cylinder block 21 and supports both ends of cylinder block 21.

Numerals 23 and 24 are the first and second elastic elements, which are provided between both end faces of cylinder block 21 and case 22 respectively. Cylinder block 21 is supported by case 22 in the direction of cylindrical axis through these elastic elements, which seal the gaps between cylinder block 21 and case 22 as well.

Numerals 25 and 26 are the third and fourth elastic elements that are provided between both parts of the outer cylindrical surface on both end face sides of cylinder block 21 and case 22 respectively. Cylinder block 21 is supported by case 22 in the radial direction through these elastic elements, which seal gaps between cylinder block 21 and case 22 as well.

In this case, O-rings are used for the first, second, third and fourth elastic elements 23, 24, 25, and 26.

In this case, in addition, cylinder block 21 is supported by first and second concavities 27 and 28 provided in case 22 through first, second, third, and fourth elastic elements 23, 24, 25, and 26.

In the above configuration, as shown in FIG. 5, a sample gas is introduced into cylinder block 21, passes along the inner and outer cylindrical surfaces of cylindrical resonator 5, and is discharged from case 22.

The density of the sample gas can be determined by measuring the resonance frequency of cylindrical resonator 5 utilizing the fact that the resonance frequency of cylindrical resonator 5 varies with the density of the gas surrounding cylindrical resonator 5.

As described above, cylinder block 21 is supported by case 22 through first, second, third, and fourth elastic elements 23, 24, 25, and 26.

As a result, (1) As described above, cylinder block 21 is supported by case 22 through first, second, third and fourth elastic elements 23, 24, 25, and 26, and thus is completely floating from case 22. Accordingly, a vibration gas density meter that has improved anti-vibration characteristics and that has enhanced noise immunity over a wide frequency range can be obtained.

(2) Hence, a vibration gas density meter that has lower installation cost, such as for selection of and limitation to pieces of vibration-proof rubber, anti-vibration construction, and installation locations, and for plastic piping work, can be obtained without requiring anti-vibration measures In the case of intense vibration disturbance.

(3) Cylinder block 21 is supported by case 22 through first, second, third and fourth elastic elements 23, 24, 25, and 26, and thus is completely floating from case 22. Thus, a vibration gas density meter that is easily electrically insulated from the ground and is ready for the adoption of intrinsically safe explosion-protected construction can be obtained by employing an electrical insulation material for first, second, third, and fourth elastic elements 23, 24, 25, and 26.

(4) If cylinder block 21 is supported by first and second concavities 27 and 28 provided in case 22 through first, second, third, and fourth elastic elements 23, 24, 25, and 26, a vibration gas density meter whose cylinder block 21 is securely supported by case 22 can be obtained.

(5) If O-rings are used for first, second, third, and fourth elastic elements 23, 24, 25, and 26, cylinder block 21 can be heat-insulated from case 22, and thus a vibration gas density meter that has good temperature characteristics can be obtained.

(6) If O-rings are used for first, second, third, and fourth elastic elements 23, 24, 25, and 26, the construction can be made simple, and thus a vibration gas density meter that has lower manufacturing cost can be obtained.

Consequently, according to the present invention, a vibration gas density meter that has improved anti-vibration characteristics, and which requires no specific vibration measures and can easily adopt the intrinsically safe explosion-protected construction, can be obtained.

Second, numeral 31 shows an introduction pipe, one end of which is connected to the sample gas entry end of cylinder block 21 and the other end of which is connected to case 22. This introduction pipe introduces the sample gas into cylinder block 21 as well as prevents heat transfer from case 22 to cylinder block 21 by having a predetermined length.

Numeral 32 shows a heat-insulation composed of heat insulating material provided around introduction pipe 31.

In the above configuration, cylinder block 21 is supported by case 22 through first, second, third, and fourth elastic elements 23, 24, 25, and 26.

In addition, heat transfer from case 22 on the sample gas entry side to cylinder block 21 is greatly reduced by introduction pipe 31.

Further, heat transfer is from case 22 on the sample gas entry side to cylinder block 21 by heat insulation 32.

As a result, (1) Cylinder block 21 is supported by case 22 through first, second, third, and fourth elastic elements 23, 24, 25, and 26, and thus is completely floating from case 22. At the same time, heat transfer from case 22 on the sample gas entry side to cylinder block 21 is greatly reduced by introduction pipe 31. Therefore, cylinder block 21 is heat-insulated from case 22 and so a vibration gas density meter that has improved temperature characteristics can be obtained.

Specifically, a vibration gas density meter in which the transient characteristics at sudden temperature changes are greatly improved and which can enhance the control characteristics in various applications, especially in calorie control for city gas, can be obtained.

(2) Accordingly, if ambient temperature changes are large, it is no longer necessary to take specific heat-insulation measures, for example, such as housing the meter in a thermostatic oven, installing the meter in anti-freeze solution, or installing the meter in an air-conditioned room. Thus, a vibration gas density meter that has lower installation cost is obtained.

(3) Cylinder block 21 is supported by case 22 through first, second, third and fourth elastic elements 23, 24, 25, and 26, and thus is completely floating from case 22. Thus, a vibration gas density meter that is easily electrically insulated from the ground and is ready for the adoption of intrinsically safe explosion-protected construction can be obtained by employing an electrical insulation material for first, second, third, and fourth elastic elements 23, 24, 25, and 26.

(4) If cylinder block 21 is supported by first and second concavities 27 and 28 provided in case 22 through first, second, third, and fourth elastic elements 23, 24, 25, and 26, a vibration gas density meter whose cylinder block 21 is securely supported by case 22 can be obtained.

(5) If O-rings are used for first, second, third, and fourth elastic elements 23, 24, 25, and 26, cylinder block 21 can be heat-insulated from case 22, and thus a vibration gas density meter that has good temperature characteristics can be obtained.

(6) If O-rings are used for first, second, third, and fourth elastic elements 23, 24, 25, and 26, the construction can be made simple, and thus a vibration gas density meter that has lower manufacturing cost can be obtained.

(7) If heat insulation 32 is provided around introduction pipe 31, heat transfer from case 22 on the sample gas entry side to cylinder block 21 is prevented. Thus, a vibration gas density meter that has improved temperature characteristics can be obtained.

Consequently, according to the present invention, a vibration gas density meter that has improved temperature characteristics, and which requires no specific heat-insulation measures and can easily adopt the intrinsically safe explosion-protected construction, can be obtained.

Third, numeral 42 is a resistance element arranged in the vicinity of open end 51 of cylindrical resonator 5.

In this case, resistance element 42 is located close to the downstream of open end-surface 511 of cylindrical resonator 5.

In the above configuration, since the heat capacity of the sample gas is small, the sample gas exchanges heat with cylindrical resonator 5 when it passes along the inner and outer cylindrical surfaces of cylindrical resonator 5. Therefore, the temperature of the sample gas becomes equal to the temperature of cylindrical resonator 5 at its open end 51.

Also, while the sample gas is passing, resistance element 42 can detect the temperature change of cylindrical resonator 5 due to inflow of heat from the outside.

As a result, (1) The resistance thermometer is mounted on the cylindrical surface of cylinder block 21 and resistance element 42 is arranged in the vicinity of open end 51 of cylindrical resonator 5. Thus, a vibration gas density meter that can detect the changes in ambient temperature and can appropriately compensate for the ambient temperature can be obtained.

(2) In addition, if resistance element 42 is arranged close to the downstream of open end surface 511 of cylindrical resonator 5, changes in ambient temperature can also be detected. Further, since temperatures are measured in a position where temperatures of cylindrical resonator 5 and the sample gas just balance, a vibration gas density meter that can detect ambient temperature changes and further can compensate for the ambient temperature accurately and appropriately, can be obtained.

Consequently, according to the present invention, a vibration gas density meter that has improved ambient temperature characteristics can be obtained.

Fourth, numeral 61 shows the predetermined number of outside flow ways of the resonator. They are provided through bottom block 41 of the cylinder block so that a stagnant portion of the sample gas is not generated when the sample gas is supplied to the outer cylindrical surface of cylindrical resonator 5. In this case, eight outside flow ways of resonator 61 are provided.

Numeral 62 is a sample gas introduction way through which the sample gas is introduced. Its one end is provided at case 22 on bottom block 41 side of cylinder block 21 and its other end is communicated with the above inside flow way of resonator 13 and the predetermined number of outside flow ways of resonator 61.

Numeral 63 is a sample gas discharge way through which the sample gas is discharged. Its one end is provided at case 22 on the opposite side of cylinder block 21 to bottom block 41 and its other end is communicated with the above opposite side of cylinder block 21 to bottom block 41.

In the above configuration, as shown in FIG. 5, the sample gas is introduced into cylinder block 21 through sample gas introduction way 62 and branched to inside flow way of resonator 13 and eight outside flow ways of resonator 61. The sample gas is then discharged from sample gas discharge way 63 after passing along the inner and outer cylindrical surfaces of cylindrical resonator 5.

As a result, (1) Outside flow ways of resonator 61 are provided through bottom block 41 of cylinder block 21 by the predetermined number so that a stagnant portion of the sample gas is not generated when the sample gas is supplied to the outer cylindrical surface of cylindrical resonator 5. Accordingly, contamination of the sample gas is eliminated, and thus a vibration gas density meter that has improved response characteristics and high sensitivity can be obtained.

(2) Provision of the inlet and outlet of the sample gas close to each other is abandoned so that the density meter can be directly inserted into a measurement piping, and sample gas introduction way 62 is provided on the one end side of cylinder block 21 and sample gas discharge way 63 is provided on the other end side of cylinder block 21. Since, as shown above, turn-back of the sample gas passage is discontinued, the passage resistance decreases and so the pressure loss is reduced.

Further, since a predetermined number of outside flow ways of resonator 61 that do not generate a stagnant part of the sample gas are provided, the pressure loss is further reduced.

For this reason, gas density can be measured even if the differential pressure between the input and output of a vibration gas density meter is small. So, since a vibration gas density meter can be placed in a cycling system for a measuring object, a specific sampling system becomes unnecessary. Thus, a vibration gas density meter that has lower installation cost can be obtained.

In particular, a vibration gas density meter suitable for measurement of dangerous sample gas can be obtained, for example, for measuring the concentration of hydrogen in hydrogen-cooled generators.

(3) Furthermore, since the pressure loss in the vibration gas density meter is small, gas density can be measured even if the differential pressure between the input and output of a vibration gas density meter is small. This eliminates the necessity to keep the sample gas at the output of a vibration gas density meter at low pressure. Thus, the sample gas whose measurement has finished can be easily returned to a place where the fluid can be reused, and does not need to be disposed of by being vented into the atmosphere as an exhaust gas, and thus is consistent with the recent trend toward protection of the global environment. Hence, a vibration gas density meter that has lower operation cost can be obtained.

Specifically, for example, a vibration gas density meter suitable for an application that, in a calorie adjustment line for liquefied natural gas (LNG), LNG after being used for measurement can be returned to a line from which the LNG was sampled, can be obtained.

Consequently, according to the present invention, a vibration gas density meter that has improved sensitivity and lower pressure loss can be realized.

What is claimed is:

1. A vibration gas density meter comprising:
   a cylindrical resonator;
   a cylinder block concentrically incorporating said cylindrical resonator so that one end of said cylindrical resonator is fixed to a bottom block of said cylinder block in a cantilever-like manner and another end of said cylindrical resonator is open ended;

vibratory means for exciting said cylindrical resonator;

an inside flow way provided for said cylindrical resonator having a cross section which is ring shaped and is provided at said bottom block of said cylinder block for supplying a sample gas to an inner cylindrical surface of said cylindrical resonator;

one or more outside flow ways provided for said cylindrical resonator through said bottom block of said cylindrical block and arranged on an outside circumference of said inside flow way and avoiding said vibratory means for supplying sample gas to an outer cylindrical surface of said cylindrical resonator;

a case concentrically incorporating said cylinder block including both ends thereof;

first and second elastic elements disposed between both ends of said cylinder block and said case, respectively, so that said cylinder block is supported by said case in a cylindrical axis direction and that gaps between said cylinder block and said case are sealed by said first and second elastic elements; and third and fourth elastic elements disposed between outer cylindrical surfaces on both end face sides of said cylindrical block and said case, respectively, so that said cylinder block is supported by said case in a radial direction and that gaps between said outer cylindrical surfaces of said cylinder block and said case are sealed, whereby said cylindrical resonator and said cylindrical block are held in a free-standing ambient vibration free and noise free position within said case; and whereby sample gas is introduced at one end of said inside flow way and split to flow into said one or more outside flow ways so as to eliminate contamination of sample gas and to enable a more accurate measurement of the sample gas without said sample gas being diverted in direction.

2. The meter of claim 1, further comprising an introduction pipe having a predetermined length and two ends, one end connected to a sample gas introducing port side of said cylinder block, and another end connected to said case, wherein said introduction pipe introduces said sample gas into said cylinder block and prevents heat transfer from said case to said cylinder block.

3. The meter of claim 1, further comprising first and second concavities provided at both end faces of said case, respectively, and wherein said first and second elastic elements are provided between said first and second concavities and said cylinder block, respectively, and through which said cylinder block is supported by said case in said cylindrical axis direction for sealing gaps between said first and second concavities and said cylinder block; and wherein said third and fourth elastic elements are provided between both parts of a cylindrical surface on both end face sides of said cylinder block and said first and second concavities, respectively, and through which said cylinder block is supported by said case in said radial direction for sealing gaps between said cylinder block and said first and second concavities.

4. The meter of claim 2, further comprising first and second concavities, respectively, and wherein said first and second elastic elements are provided between said first and second concavities and said cylinder block, respectively, and through which said cylinder block is supported by said case in said cylindrical axis direction for sealing gaps between said first and second concavities and said cylinder block, and wherein said third and fourth elastic elements are provided between both parts of a cylindrical surface on both end face sides of said cylinder block and said first and second concavities, respectively, and through which said cylinder block is supported by said case in said radial direction for sealing gaps between said cylinder block and said first and second concavities.

5. The meter of claim 1, 2, 3 or 4 wherein said first, second, third and fourth elastic elements comprise O-rings.

6. The meter of claim 1, 2, 3 or 4, further comprising heat insulating material provided in part of all of said gaps between said cylinder block and said case.

7. The meter of claim 1 or 4, further comprising heat insulating material provided around said introduction pipe.

8. The meter of claim 1, further comprising a resistance thermometer mounted on a cylindrical surface of said cylinder block and comprising a resistance element arranged in vicinity of said open end of said cylindrical resonator.

9. The meter of claim 8, wherein said resistance element is arranged in vicinity of a down side stream side of said open end of said cylindrical resonator.

10. The meter of claim 1, wherein said one or more outside flow ways are provided through said bottom block of said cylinder block in a predetermined number so that a stagnant part of said sample gas is not generated when said sample gas is supplied to said outer cylindrical surface of said cylindrical resonator; and wherein said sample gas is introduced through an introduction way having one end thereof at said case on a bottom block side of said cylindrical block and another end thereof communicated with said predetermined number of outside flow ways and said inside flow way; and wherein said sample gas is discharged through a discharge way having one end thereof provided at said case on a side opposite said bottom block side of said cylinder block and another end thereof communicated with a port on a side of said cylinder block.

* * * * *